United States Patent [19]

Reich

[11] Patent Number: 5,674,488
[45] Date of Patent: Oct. 7, 1997

[54] METHOD FOR PREVENTION AND TREATMENT OF HYPERCHLOLESTEROLEMIA BY IN VIVO HYDROGENATION OF CHOLESTEROL

[76] Inventor: John J. Reich, 3N 550 Crown Rd., Elmhurst, Ill. 60126

[21] Appl. No.: 319,818

[22] Filed: Oct. 7, 1994

[51] Int. Cl.⁶ .......................... A61K 38/44; A61K 31/59; A61K 31/40
[52] U.S. Cl. .......................... 424/94.4; 514/167; 514/410; 514/824
[58] Field of Search .................... 514/167, 410, 514/824; 424/94.4

[56] References Cited

U.S. PATENT DOCUMENTS

| | | | |
|---|---|---|---|
| Re. 30,910 | 4/1982 | Wigand | 514/182 |
| 2,697,106 | 12/1954 | Shepherd et al. | 552/544 |
| 2,813,879 | 11/1957 | Wildi et al. | 552/547 |
| 2,838,526 | 6/1958 | Laubach | 552/544 |
| 2,840,574 | 6/1958 | Chemerda et al. | 552/547 |
| 2,979,440 | 4/1961 | Smythe | 435/187 |
| 3,859,437 | 1/1975 | Wigand | 514/177 |
| 3,959,540 | 5/1976 | Liberich et al. | 428/35 |
| 4,001,480 | 1/1977 | Shank | 428/411 |
| 4,009,076 | 2/1977 | Green et al. | 435/187 |
| 4,106,991 | 8/1978 | Markussen et al. | 435/187 |
| 4,231,938 | 11/1980 | Monaghan et al. | 519/292 |
| 4,251,387 | 2/1981 | Lim et al. | 252/316 |
| 4,351,844 | 9/1982 | Patchett et al. | 514/460 |
| 4,362,711 | 12/1982 | Cerami | 429/497 |
| 4,482,630 | 11/1984 | Allen et al. | 435/187 |
| 4,492,706 | 1/1985 | Kallai-Sanfacon | 514/365 |
| 4,603,142 | 7/1986 | Burger et al. | 514/456 |
| 4,689,326 | 8/1987 | Hall et al. | 514/217 |
| 4,778,791 | 10/1988 | Takashima et al. | 514/211 |
| 4,797,278 | 1/1989 | Kawai et al. | 424/93.44 |
| 4,812,441 | 3/1989 | Kawai et al. | 514/2 |
| 4,877,778 | 10/1989 | Carpenter et al. | 514/58 |
| 4,921,710 | 5/1990 | Beitz et al. | 426/56 |
| 5,028,599 | 7/1991 | Hunter | 514/83 |
| 5,032,608 | 7/1991 | Dudrick | 514/396 |
| 5,106,836 | 4/1992 | Clemens et al. | 514/21 |
| 5,114,963 | 5/1992 | Holaday et al. | 514/443 |
| 5,436,004 | 7/1995 | Beitz | 424/94 |

OTHER PUBLICATIONS

Li et al., "Hypocholesterolemic effect of *Eubacterium coprostanoligents* ATCC 51222 in rabbits," *Letters in Applied Microbiology*, 20, pp. 137–140 (1995).

Ashes et al., "Ruminal hydrogenation of cholesterol", *J. Lipid Res.*, 19:244–249 (1978)(.

Byun et al., "Effect of Cholestanol Feeding on Sterol Concentrations in the Serum, Liver, and Cerebellum of Mice", *J. Biochem.*, 103(2):375–379 (1988).

Iowa State University – Iowa Agriculture and Home Economics Experiment Station Annual Report, "Lagoon Find Helps Cholesterol Project", pp. 8–9 (1991).

Kannel and Thom, "Declining cardiovascular mortality", *circulation*, 70(3):331–336 (Sep.1984).

Greg Brown, et al., Regression of Cornary Artery Disease As a Result of Intensive Lipid Lowering Threapy in Men With High Levels of Apoplipoprotein B, The New Eng. J. Med., 323(19):1289–1297. Nov. 8, 1990.

Jong B. Yang, A Fluorometric Asay for Cholesterol Reductase Activity, Analy. Biochem. 206:240–250. 1992.

*Primary Examiner*—John W. Rollins
*Attorney, Agent, or Firm*—Marshall, O'Toole, Gerstein, Murray & Borun

[57] ABSTRACT

A method for lowering blood cholesterol levels which comprises administering to a human suffering from hypercholesterolemia an effective amount of a delta 5 hydrogenating enzyme over an extended period of time sufficient to effect a reduction of the blood cholesterol level of said human.

10 Claims, No Drawings

METHOD FOR PREVENTION AND TREATMENT OF HYPERCHLOLESTEROLEMIA BY IN VIVO HYDROGENATION OF CHOLESTEROL

BACKGROUND OF THE INVENTION

1. Field of Invention

The present invention is directed to a method for lowering blood cholesterol and treatment of diseases associated with hypercholesterolemia, including atheriosclerosis. More particularly, the present invention is directed to a method for hydrogenating both dietary and endogenous cholesterol into dihydrocholstrol in the small intestine by the oral administration of a delta 5 hydrogenating enzyme.

2. Description of Related Art

It has been known for over one hundred years that plaque deposited in the arteries of man and other animals have consisted mostly of cholesterol. Many epidemiological studies have shown that people with high levels of blood cholesterol are at high risk of developing arterial diseases. Hypercholesterolemia, as the condition is known medically, is also known to be a prime risk factor for Cardiovascular Disease (CVD), such as arteriosclerosis. Atherosclerosis, the most serious form, is a disease of the large and medium-size arteries. Cardiovascular Heart Disease (CHD) is the most lethal form and is recognized to be the leading cause of death in the United States. Kannel, W. B., Thom, T. J., "Declining Cardiovascular Mortality", Circulation 70:331–336 (1984). It afflicts over 6 million Americans and costs over 60 billion dollars a year in direct and indirect medical cost relating to cardiac infarction. "National Institutes of Health Consensus Development Conference On Lowering Blood Cholesterol to Prevent Heart Disease," JAMA:253, No. 14, 2080–2086 (1985). Secondary physiological effects, which often accompany the onset of atherosclerosis, include cerebral strokes, sub-optimal liver function, renal artery blockage, senility, male impotence, arteriosclerotic aneurysms and limb gangrene. In addition to cholesterol deposits in arterial walls (atheromas) there are deposits in skin and tendons known as xanthomas.

It is believed the sequence leading to the disease is the formation of fatty streaks in the aorta, carotid, coronary, and cerebral and peripheral arteries. These lesions are due to lipid deposits, principally cholesterol, in the innermost vessel wall or intima layer, resulting from the uptake of cholesterol from the blood. A fibrous plaque development stage follows with the accumulation of white blood cells (macrophages), extra cellular lipids (free cholesterol), cellular debris and collagen over which smooth muscle cells form a cap. Advanced lesions become calcified resulting in a loss of elasticity (hardened arteries) and obstruction of blood flow (ischemia) often exceeding a 75% blockage before being detected. The plaque is subject to fractures with resultant blood clot formation (thrombosis) as evidence by incidences of myocardial and cerebral infarctions commonly recognized as heart attacks and stokes. Atherosclerosis is also the origin of most chest pain (angina) and is responsible for some kidney and liver failures.

Recently there has been a renewed emphasis on lowering blood cholesterol particularly the Low Density Lipoprotein (LDL) faction, the major reservoir of cholesterol in blood plasma. The upper level to be considered normal (non pathogenic) is not well established but is certainly lower than the average U.S. level of 210 mg/dl (miligrams per deciliter) and by some it is believed to approach 100 mg/dl. Consequently large segments of the Western population are at a high risk of developing CVD and are thus considered to be suffering from hypercolestrolemia.

Other conditions exacerbate the importance of maintaining low cholesterol levels, e.g. hypertension, diabetics, smoking, age, physically inactive life styles and male gender; making a successful long term treatment for hypercholesterolemia of exceptional medical importance.

Many attempts have been made to lower the blood cholesterol level in man through dietary management, behavior modification, exercise and drug therapy aimed at reducing or controlling the blood cholesterol levels. The first recommendation in treating hypercholesterolemia is generally dietary intervention, whereby lipid intake has been restricted.

Dr. Dean Ornish et. al. "Can Lifestyle Changes Reverse Coronary Heart Disease," *The Lancet*, vol. 336 (1990) and his ongoing program for reversing heart disease, has shown that complete elimination of dietary cholesterol and limiting fat content to less than ten percent of the daily caloric intake can effect a four percent regression of atherosclerotic plaque after five years when combined with stress management and aerobic exercise. This strict vegetarian diet (free of meat, fish, chicken, vegetable oils and all dairy fat products) is unrealistic for all but the most severely dedicated individuals.

Less severe diet restrictions have failed to stop atherosclerosis progression. The American Heart Association recommends 30% of daily caloric intake from fat, but it is also recognized not to be effective in preventing the onset of CVD in most individuals. Phase II guidelines of 20% of daily caloric intake from fat for heart patients as referenced by the University of Chicago Hospitals 1992 publication "Heart-Mend A New Way To Counter Coronary Artery Disease" has failed to arrest the progression of the diseases.

A variety of dietary supplements or specific foods e.g. brans, psylliums, guar gum, lecithins, whey, red wines, fish oils and ginseng root extract have been reported to reduce high blood cholesterol or its consequences. The mechanisms are varied and include cholesterol sequestering, chelating, entrapment and oxidation inhibition. Such regimens generally affect only less than ten percent reduction in blood cholesterol. None of these dietary interventions have been shown to arrest or cure atherosclerosis or other high blood cholesterol associated diseases.

The most severe dietary intervention has been reported in U.S. Pat. No. 5,032,608 where it describes intravenous feeding of a mixture of biologically active levorotatory amino acids which replace all other feedings except water. Reductions of fifty percent were noted in both blood cholesterol levels and atherosclerotic plaque over a six month period of treatment in a hypercholesterolemia patient and in other "normal" intravenous nourished patients.

A functionally equivalent fat free dietary composition is described in U.S. Pat. No. 5,106,836 which discloses a method for preparing enteral food products with a modified fat free total parenteral nutritional amino acid formulation. The prepared foods, when digested and absorbed, deliver an amino acid profile into the blood having hypocholestrolemic properties. It is reported that a significant reduction in total plasma cholesterol and regression of atherosclerosis is shown if the diet is maintained.

Other attempts to lower serum cholestrol levels have been attempted through various pharmaceutical preparations. For example, a bacterial cell product has been reported in U.S. Pat. No. 4,797,278 to lower blood cholesterol and/or triglyceride levels by having the ability to adhere to intestinal epithelial cells of the intestine thereby optimizing the conditions for colonization of beneficial bacteria in the appropriate areas in the intestine. It further indicates that blood triglycerides (free of delta 5 carbons) are also reduced in concentration. In fact, the triglyceride levels are reported to be lowered substantially more than the cholesterol levels. The mechanism involved is not described, however, it is noted that triglycerides have no delta 5 carbon to hydrogenate as does cholesterol. Furthermore, the hydrogenation of triglycerides does not substantially decrease their digestion. This demonstrates that some mechanism other than hydrogenation is involved for the reduction of serum cholesterol concentration as disclosed in this method.

U.S. Pat. No. 4,812,441 discloses cholesterol-reducing proteins derived from the streptococcus bacterium described above and being the same as those belonging to the identical class of known microorganism. Streptococcus derived proteins have no known cholesterol hydrogenating enzymatic activity. Thus the reported cholesterol reducing activity of the protein derived from the above bacteria must also rest with some other mechanism other than hydrogenation of the delta 5 carbon of cholesterol.

U.S. Pat. No. 5,114,963 describes a method of reducing atherosclerotic disease by reducing serum levels of lipoprotein by the administration of N,S-diacryl-L-cystein.

U.S. Pat. No. 4,231,938 describes cholesterol reducing compounds cultivated from the microfungus Aspergillus for the treatment of atherosclerosis and hyperlipemia. These compounds have been found to inhibit cholesterol biosynthesis in the body, thereby reducing cholesterol levels. These compounds do not hydrogenate cholesterol into dihydrocholesterol.

Methods of treating myocardial damage have also centered on the intravenous injection of compounds in combination with fibrinolytic enzymes to digest or dissolve blood thrombosis, lysing fibrin clots and re-establishing and maintaining perfusion of ischemic tissue. This use of enzymes, whose amelioration of the consequence of atherosclerosis is described in U.S. Pat. No. 5,028,599, does not lower blood cholesterol concentration.

In view of the above failures of dietary, enzyme therapy and lifestyle interventions, other means have been sought to lower blood cholesterol, reverse arterial plaque deposits and otherwise mitigate its effects on other tissue. The lowering of cholesterol with hypocholesterolemic drugs to reduce the risk of coronary heart disease is supported by convincing evidence to have a causal association. These drugs and their adverse side effects are well described in the Physicians' Desk Reference Medical Economics Company Oradell, N.J.

Of these, bile acid sequestrants e.g. cholestipol and cholestyamine (anion exchange resins), have been described in numerous publications and are generally used to treat hypercholesterolemia. This treatment seems to be moderately effective. However, these drugs must be consumed in large quantities, are non-palatable and have various intestinal side affects including nausea, indigestion, constipation and abdominal discomfort.

Cholesterol anti-absorption drugs e.g. melinamide, thioesters, substituted urea and thiourea, are also effective in inhibiting acyl CoA:cholesterol acyltransferase (ACAT) the enzyme which esterifies cholesterol as it enters the intestinal mucosal cells. However, they are less effective in lowering blood cholesterol perhaps as unesterified cholesterol is also believed to enter the blood stream directly.

Activated carbon (charcoal tablets) has been reported in the popular press Apr. 27, 1993 edition of the National Examiner to be effective in absorbing cholesterol and reducing serum cholesterol as much as 43 percent citing Dr. Saul Hendler's, University of California, San Diego book "The Doctors' Vitamin and Mineral Encyclopedia". However, charcoal is reported by the same author to bind vitamins and drugs and thus is a concern for these reasons. The catalyst of the present invention is cholesterol specific and has no such effect on vitamin or drug absorption.

U.S. Pat. No. 4,877,778 describes intravenous injections of certain cyclodextrins that act as substitute apoproteins cholesterol carriers. While only slightly reducing blood cholesterol they are purported to redistribute lipid-soluble materials, e.g. vitamin A and cholesterol between tissue and blood thus mitigating the effects of excess cholesterol or oleophilic vitamin poisoning. They have, however, failed to arrest atherosclerosis or other cholesterol depositing diseases.

U.S. Pat. No. 4,351,844 describes hydrogenation of certain described compounds which are subsequently administered orally or parenterally to reduce cholesterol levels. The hydrogenation of the described compounds over various catalysts produces dihydro and tetrahydro products. The mechanism described is to inhibit the body's ability to synthesize cholesterol.

There are numerous other cholesterol biosynthesis limiting drugs such as Lovastatin and its analogs; Fluvastatin, Simvastatin and Pravastatin. These seem to be more effective in reducing blood cholesterol by inhibiting HMG-CoA reductase, (3-hydroxy-3-methylglutaryl-coenzymeA) the enzyme affecting the rate limiting step in cholesterol biosynthesis. However, they have many adverse side effects including liver impairment. This is especially critical when liver functions have oftentimes already been compromised from hypercholesterolemia. These drugs are also generally not long tolerated and have no effect on the uptake of cholesterol from the intestines.

Mevinolin and Compactin and their analogs resemble HMG-CoA, the substrate of HMG-CoA reductase, but long term side effects are unknown. Thus, their use is limited to familial hypercholesterolemia investigations. Less effective are drugs that inhibit other cholesterol biosynthesis steps involving HMG-CoA reductase and lanosta-8,24-diene-3b-ol 14a-methyl-dimethylase, e.g. oxygenated and substituted lanosterols.

A recent attempt to lower blood cholesterol levels by chemical means other than interfering with cholesterol biosynthesis has been disclosed in U.S. Pat. No. 4,921,710. There, cholesterol reductase, an enzyme which catalytically hydrogenates cholesterol in the delta 5 position, has been proposed as a means of decreasing cholesterol concentration in cell membranes of the muscle of meat source animals, fish, eggs and milk products prior to consumption by man. For example, intravenous injections of cholesterol reductase are administered to livestock just before slaughter "preferably within one hour of slaughter, commonly within 30 minutes of slaughter, and in every instance at least 15 minutes before slaughter." The enzyme preparation converts cholesterol to coprostanol in the animal, thus decreasing the amount of cholesterol in the foodstuff before ingestion. However, dosages are such to hydrogenate the cholesterol in the animal or foodstuff but does not hydrogenate the serum cholesterol already present in man once the food stuff is digested. This method of removal of cholesterol from foodstuff is of little value in preventing, treating or curing the ravages of hypercholesterolemia as are other means wherein foodstuffs have their cholesterol content physically removed, e.g. with solvents or starches.

Other drug therapy regimes have also been used in an attempt to lower blood cholesterol. Proposed administration of prolactin inhibiting drugs, i.e. ergot-related compounds, to indirectly reduce lipid synthesis and thereby cure hypercholesterolemia and atherosclerosis, have been unconvincing and have many adverse side affects such as interference with lactation, anti-fertility, weight loss, among other side effects.

Nicotinic acid has long been known to be moderately effective in reducing blood cholesterol. It specifically reduces elevated Very Low Density Lipoprotein (VLDL), Low Density Lipoprotein (LDL) and Intermediate Density Lipoprotein (IDL). However, it's side effects are cutaneous flush, pruritus, arterial fibrillation, gastrointestinal irritation, hepatotoxicity and cardiac arrhythmias and results in poor patient compliance with prescribed doses. The contraindication of niacin with hepatic dysfunction, a near certainty concomitant with hypercholesterolemia, marginalizes it's use. The mechanism of lowering cholesterol is by increasing cholesterol excretion in bile acids and thus its use in combination with cholesterol sequestering drugs to lower its reabsorption.

Probucol has a moderate effect in reducing LDL but it also reduces HDL (High Density Lipoprotein) and remains in the adipose tissue for months after treatment ceases. Side effects include diarrhea, nausea and other gastrointestinal stresses and has experimentally been shown to induce cardiac arrhythmias. It is believed that LDL transports cholesterol to the arterial walls for deposit whereas HDL carries it away hence the concern with drugs which reduce HDL cholesterol.

Clofibrate, as with other fibrates, such as bezanbrate and gemfibrozil, previously considered effective in lowering blood cholesterol and/or raising HDL is now of questionable effectiveness and coupled with its serious latent flu-like side effects its use too has been marginalized.

An increasing interest exists for drugs that can increase blood HDL. One of these drugs is 8-chlorobenzothiazepine which has been reported in U.S. Pat. No. 4,778,791 to improve the balance between HDL and LDL. It is believed to be beneficial because high levels of high density lipoprotein have been associated with decreased incidence of ischemic heart disease. However, the associated improvement with high levels of HDL disappears below a 150 mg/dl level of total cholesterol. Thus this approach may only be beneficial in severe hypercholesterolemic patients. Consequently, the principal benefit of the drug therapy may be with its hypotensive and vasodilating properties. Other reported HDL raising drugs are similarly limited in applicability.

Nitrates, calcium channel blockers, beta blockers and certain herb extracts have been variously reported to lower, raise or leave unchanged blood cholesterol levels. All lower blood pressure and generally reduce deaths due to CVD. Their cardiac oxygen demand lowering and hypotensive activity are their principal merit. However, they do not appear to have any anti-atherosclerotic property.

Vascodilators such as pentoxifylline, a synthetic analog of caffeine, has been proposed as a treatment of CVD. It promotes increased cardiac blood flow without lowering blood cholesterol. When intravenously injected the increased blood flow to ischemic limbs, heart and liver has a resultant improvement in micro-circulation by virtue of increasing red blood cell (erythrocyte) flexibility. The seriousness of its side effects are unknown but highly suspicious as the severely decreased blood viscosity resulting from its anti-fibrinogen effect can affect bleeding. This is especially disturbing because it also has a inhibiting effect on platelet aggregation.

Khellin, also a vasodilator, is purported to be an effective anti-atherosclerotic but has anti-spasmodic activity extending to urethra, bronchial and intestinal passageways and central nervous system depressant activity. This severely limits its suitability for treatment of arteriosclerosis.

Vitamin E as well as other antioxidants, including probucol, appear to inhibit the genesis of atherosclerosis because oxidized LDL may be more likely to initiate the accumulation of cholesterol in monocytes and macrophages which eventually become deposited in the arterial plaque. However, it has little benefit in actually preventing the disease or slowing its progression and recommended large dosages have their own dangers.

Once drug therapy has been found to be ineffective in treating atherioscerosis and like diseases, the next treatment is usually through surgical means by removing the worst deposits in the coronary and carotid arteries. Non-plaque removal method which circumvent the arterial blockage include angioplasty and coronary bypass surgery. All of these procedures are expensive, involve considerable risk and do not arrest or reverse the progress of the disease. The disease usually returns to its pre-operative condition in less than ten years. These procedures create a significant risk of morbidity and mortality associated with surgery. Furthermore, it has not been shown that there is a statistical benefit in the survival rate or rate of development of the disease between surgically and medically treated patients.

Therefore, in view of the above, it is clear from the extensive research in the treatment of physiological conditions believed to be caused by high dietary fat and cholesterol that induce atheromatous lesions, fatty cirrhosis and other xanthomas, that strong interest exists for an effective means for lowering blood cholesterol. It is also clear that the average blood cholesterol levels in Western culture is hypercholesterolemic and levels below 100 mg/dl will be required to reverse these diseases. As of today, present drug therapies are clearly inadequate and are accompanied by serious multiple side effects. Furthermore, strict vegetarian diets are required which are unrealistic for the vast majority of people.

It is also clear that a new mechanism for reducing blood cholesterol is vitally needed and must be elucidated before these diseases can be prevented, arrested and reversed in the majority of the population. It would also be of immense value if such a mechanism would re-generate lipid tissue damage in the liver rather than cause further damage as is the case with many of the cholesterol lowering drugs.

Complications of CVD are the major cause of death in Western civilization and atherosclerosis is the primary physiological process identified in this mortality. A method of reducing and reversing these deposits which precipitate tissue damage without patient side effects would present a substantial advancement in prevention and treatment. A method which would aid in rehabilitation and cure of these injured tissues would similarly be a major advancement.

None of the above drugs alone or in combination, have been shown to significantly lower blood cholesterol and reduce artheriosclerosis plaque without requiring concurrent severe restriction on ingestion of lipids. So far there still is lacking any effective and safe drug which would prevent and treat CVD and at the same time be without any adverse side-effects.

The object of the present invention is to provide a safe and effective treatment for diseases associated with high cholesterol levels without the associated side effects and severe life style restrictions.

SUMMARY OF INVENTION

It has been discovered that oral administration of a delta 5 hydrogenating enzyme will hydrogenate both dietary and endogenous cholesterol in the small intestine of man into dihydrocholesterol. The conversion of cholesterol into dihydrocholestrol will prevent cholesterol absorption or reabsorption into the blood stream and effect a reduction of serum cholesterol to sub-normal levels. The resultant hypocholestolemia caused by the use of a delta 5 hyrogenating enzyme will also deplete arterial plaque of its cholesterol over a sufficient period of time when used in combination with other cholesterol reducing therapy drugs. Accordingly, it is an object of this invention to provide a safe and effective method for treating diseases associated with hypercholesterolemia by lowering blood cholesterol levels. It is also a further object of this invention to provide a safe and effective method for arresting or reversing the buildup of arterial plaque in the arteries without the many side effects of conventional drug treatments and further eliminate or reduce the need for severe diet and lifestyle changes. The present invention also effectively removes cholesterol in the body without resorting to food processes which may decrease the palatability, taste or texture of the food and without the expense of an additional food process.

DETAILED DESCRIPTION OF THE INVENTION

The present inventor has found that dietary and endogenous cholesterol can be hydrogenated in the small intestine of man by the oral administration of a delta 5 hydrogenating enzyme over an extended period of time. The discovery that a delta 5 hydrogenating enzyme can be used in an oral preparation to reduce cholesterol to dihydrocholesterol in the body is believed to be new.

The delta 5 hydrogenating enzyme catalyzes the chemical reduction of the double bond at the delta 5 position on the cholesterol molecule. Reduction of the double bond gives rise to dihydrocholestrol e.g. coprostanol and cholestanol, both which are naturally occurring in the body. Coprostanol and cholestanol are poorly absorbed by the gastrointestinal tract and are excreted from the body and found abundantly in the feces. By reducing cholesterol into dihydrocholestrol, it will prevent the absorption of both dietary and endogenous source cholesterol into the bloodstream.

The method of cholesterol absorption from the intestines is believed to be effected by an active transfer means in that the mucosal membrane which selectively absorbs cholesterol but does not absorb cholestanol or coprostanol (dihydrocholesterol). It is believed that typically eighty percent of the cholesterol found in man is absorbed or reabsorbed whereas only five percent of the hydrogenated cholesterol (dihydrocholesterol) is absorbed. It is this physiological distinction between cholesterol and dihydrocholesterol that is believed to be the principle mechanism by which blood cholesterol levels are lowered by the teaching of this invention. By hydrogenating cholesterol before its absorption in the body, the amount of dietary cholesterol thwarted from absorption is believed to be typically up to 500 milligrams daily. Endogenous cholesterol so diverted is believed to be typically about 1000 milligrams daily. Thus, a combined diversion of cholesterol from absorption/ reabsorption equals forty percent of the total daily serum cholesterol uptake.

The hydrogenation of dietary and endogenous cholesterol, in turn, will prevent the body's natural mechanism of depositing and accumulating excess cholesterol in the blood vessels, arteries and other body pools. It is known that the elimination or lowering of cholesterol from the bloodstream will cause the body naturally to deplete or withdraw the previously deposited excess cholesterol from the various body pools.

Moreover, conditions such as atherosclerosis may also be arrested or reversed. It is believed that administration of a delta 5 hydrogenating enzyme in combination with HMG CoA reductase inhibitor [e.g., lovastatin] or other cholesterol reducing therapy drugs will not only lower blood cholesterol levels but further reverse or reduce the accumulation of arterial plaque in the arteries when used over an extended period of time.

The delta 5 hydrogenating enzymes of this invention may be orally administered to a hypercholesterolemia patient in a daily amount of at least 10 to about 100 miligrams. In the practice of the invention, satisfactory results can be obtained when up to 3,000 mg per day of the delta 5 hydrogenating enzyme is administered to the hypercholesteremic patient being treated, while the optimum daily dosage appears to be about 150 to 750 mg per day, although other dosage levels can give beneficial results. Typically, the hydrogenating enzyme is administered three to four times a day.

When administering the delta-5 hydrogenating enzyme with HMG-CoA reductase inhibitor the daily dose of the delta 5 hydrogenating enzyme and the HMG-CoA reductase inhibitor will be about 20 mg to 40 mg q.i.d. (four times a day) for the delta 5 hydrogenating enzyme and about 20 mg to 40 mg q.i.d. (twice a day) for the HMG-CoA reductase inhibitor. Typically, the ratio of the delta 5 hydrogenating enzyme to HMG-CoA reductase inhibitor for daily administration is 2 to 1. Best results can be achieved when the total dosage is in the range of 150 mg.

However, the dose required depends on many factors which affect blood cholesterol and dietary lipid levels, such as, severity of CVD, age and weight and a host of other interactions with the catalyst activity constant, dissipation rate and rates of hydrogenation. In general, the desired dose in oral administration can be in excess of the daily dosage to insure near complete hydrogenation. However, to achieve the purpose and objective of this invention, the enzyme may be incorporated in such suitable final dosage forms as may be satisfactorily prepared and employed by one skilled in the art. Thus, the commonly employed acceptable dosage form suitable for oral administration containing the active enzyme is in sufficient concentrations to attain the desired results over an extended period of time. The pharmaceutically acceptable, non-toxic carriers usually employed for such purposes may be utilized to prepare such dosage forms as tablet, capsules, lozenges, granules, powders, solutions or suspensions.

The preferred method of oral administration is tablets or capsules of enteric coated granules containing the active delta 5 hydrogenating enzyme. However, the essential consideration is that the active enzyme reach the upper one-third portion of the small intestine in sufficient strength and activity to hydrogenate the dietary and endogenous cholesterol before it is significantly absorbed by the intestines. It is also preferred to administer the hydrogenating enzyme with meals because stomach ejections into the small intestine trigger the endogenous cholesterol contained in bile secretions, allowing both dietary and endogenous cholesterol to come into contact with the hydrogenating enzyme in the same place and time.

For enzymatic hydrogenation this is fortuitous because the concurrent rise in ph of the digested food when it enters the small intestine promotes increased activity, peaking near a ph of 7. For less than maximum effect, lower dosages or administrations less frequent than with every meal may be prescribed. This will depend on the time frame in which the enzyme remains active and in a position in the intestine to be effective.

The value of in vivo hydrogenation of cholesterol as contrasted with hydrogenation of cholesterol in food-stuff prior to ingestion is dramatic. When carried out in the small intestine both endogenous as well as dietary cholesterol is hydrogenated. Typically one thousand milligrams per day of cholesterol is excreted in the bile acids whereas, even with high fat diets, the amount of dietary cholesterol is less than five hundred milligrams. Thus the potential for decreasing blood cholesterol by intestinal hydrogenation is threefold that of food hydrogenation alone.

The delta 5 hydrogenating enzyme may also be administered parenterally. The delta 5 hydrogenating enzyme is present within a suitable aqueous solution in concentrations ranging from as low as 0.1 weight percent up to 10 weight percent. Preferably, the delta 5 hydrogenating enzyme is present within solution concentrations ranging from about 0.1 to 0.5 weight percent. The dosage may be administered about 2 times a day. Any pharmaceutical acceptable diluent, adjuvant or carrier may be used in the practice of this invention.

The principle mechanism believed, to reduce blood cholesterol by parenterally means of injection of the delta 5 hydrogenating enzyme is the increased excretion rate of hydrogenated cholesterol by the liver and lowered reabsorption rate from the intestines as compared with cholesterol.

A preferred delta 5 hydrogenating enzyme is human reductase because it is believed to populate the ascending large intestine in man. Because endogenous and dietary cholesterol are absorbed principally in the first one-third of the small intestine, it is believed that human reductase is in the wrong place at the wrong time to be effective. Thus, it is many hours after the cholesterol has been available for absorption before it comes into contact with the human reductase enzyme that could hydrogenate it.

Alternative sources of cholesterol hydrogenating enzymes may be preferred for other reasons of cost, activity, purity and availability. Thus the disclosure is more generally made to enzymes known as cholesterol dehydrogenate (reductase) which are found widely in nature from plant and bacterial sources and associated in sewage and intestines of numerous animal species and in the rumen of all ruminants. A form of cholesterol dehydrogenate, species Nocardia, is available from Scripps Laboratories, San Diego, Calif. It has also been demonstrated that fragments of some enzymes retain their hydrogenating properties leading to the realization that bioengineered proteins or amino acids may be even more effective or economically justified and thus preferred under particular circumstances and for the purpose of the appended claims of the present invention are considered as delta 5 hydrogenating enzymes. Conversely bacteria that generate hydrogenating enzymes may also be effective in vivo administration and may be preferred under certain circumstances.

Co-administration of various other regimens with the delta 5 hydrogenating enzymes is disclosed and may have value by virtue of their co-operative mechanism. Use of ACAT inhibitors (cholesterol esterifying agents) are known to lower the esterified forms of cholesterol in the deposits and such esters are known to be removed more slowly in hypocholesterolemia conditions. HMG-CoA reductase inhibitors are the preferred cholesterol reducing drug for co-administration of the delta 5 hydrogenating enzyme. Thus arteriosclerosis can be corrected more quickly by combining both therapies. Similarly, drugs which inhibit the synthesis of cholesterol can be combined with oral administration of the delta 5 hydrogenating agents for an entirely oral method of treatment. Similarly restricting fats in the diet augment the oral administration of cholesterol hydrogenating enzymes by reducing the starting materials for cholesterol biosynthesis.

The foregoing description of the preferred embodiment of the invention has been presented for the purpose of illustration and description. It is not intended to be exhaustive or to limit the invention to the precise form disclosed. Many modifications and variations are possible in light of the above teaching.

I claim:

1. A method for lowering blood cholesterol levels which comprises administering to a human suffering from hypercholesterolemia an effective amount of at least 10 milligrams of a delta 5 hydrogenating enzyme over an extended period of time sufficient to effect a reduction of the blood cholesterol level of said human.

2. A method according to claim 1 wherein the delta 5 hydrogenating enzyme is human reductase.

3. A method according to claim 1 wherein the delta 5 hydrogenating enzyme is cholesterol dehydrogenate.

4. A method for lowering blood cholesterol levels which comprises administering to a human suffering from hypercholesterolemia an effective amount of at least 10 milligrams of a delta 5 hydrogenating enzyme and a HMG-Co A reductase inhibitor over an extended period of time sufficient to effect a reduction of the blood cholesterol levels and to reverse or reduce the accumulation of arterial plaque in the arteries of said human.

5. A method according to claim 4 wherein the delta 5 hydrogenating enzyme is human reductase.

6. A method according to claim 4 wherein the delta 5 hydrogenating enzyme is cholesterol dehydrogenate.

7. A pharmaceutical composition for use in treating hypercholesterolemia in a human, said composition comprising a pharmaceutically acceptable diluent, adjuvant or carrier and an effective amount of a delta 5 hydrogenating enzyme sufficient to effect the reduction of the blood cholesterol levels of said human.

8. A pharmaceutical composition for use in treating hypercholesterolemia in a human, said composition comprising a pharmaceutically acceptable diluent, adjuvant or carrier and an effective amount of a delta 5 hydrogenating enzyme and a HMG-Co A reductase inhibitor sufficient to effect the reduction of blood cholesterol levels and to reverse or reduce the accumulation of arterial plaque in the arteries of said human.

9. A method for lowering blood cholesterol levels which comprises parenteral administration to a human suffering from hypercholesterolemia an effective amount of at least 0.1 weight percent of a delta 5 hydrogenating enzyme over an extended period of time sufficient to effect a reduction of the blood cholesterol levels and to reverse or reduce the accumulation of arterial plaque in the arteries of said human.

10. A pharmaceutical composition for use in treating hypercholesterolemia in a human, said composition comprising a pharmaceutically acceptable diluent, adjuvant or carrier and an effective amount of at least 10 milligrams of a delta 5 hydrogenating enzyme sufficient to effect a reduction of blood cholesterol levels and to reverse or reduce the accumulation of arterial plaque in the arteries of said human.

* * * * *